United States Patent [19]

Wilson

[11] Patent Number: 5,170,902

[45] Date of Patent: Dec. 15, 1992

[54] SPLASH SHIELD

[75] Inventor: Earl Wilson, Ingleside, Ill.

[73] Assignee: The Kendall Company, Mansfield, Mass.

[21] Appl. No.: 643,640

[22] Filed: Jan. 4, 1991

Related U.S. Application Data

[62] Division of Ser. No. 521,960, May 11, 1990, abandoned, which is a division of Ser. No. 238,717, Aug. 30, 1988, Pat. No. 4,932,552.

[51] Int. Cl.⁵ .............................................. B65D 41/26
[52] U.S. Cl. ............................ 220/731; 220/DIG. 21; 206/569; 206/570
[58] Field of Search ..................... 220/DIG. 21, 731; 206/569, 570

[56] References Cited

U.S. PATENT DOCUMENTS

| 1,100,536 | 6/1914 | Clarke | 220/DIG. 21 |
|---|---|---|---|
| 1,332,202 | 3/1920 | Cole | 220/255 |
| 1,753,946 | 4/1930 | Replogle | 220/255 |
| 2,661,889 | 12/1953 | Phinney | 220/90.4 |
| 2,748,946 | 6/1956 | Smith | 220/90.4 |
| 3,169,679 | 2/1965 | Hunter | 220/255 |
| 4,420,111 | 12/1983 | Hament | 220/90.4 |
| 4,516,689 | 5/1985 | Barker | 220/90.4 |
| 4,893,723 | 1/1990 | Seabolt | 220/90.4 |

Primary Examiner—Joseph Man-Fu Moy
Attorney, Agent, or Firm—Alvin Isaacs

[57] ABSTRACT

A device for performing a procedure comprising, a first tray, a second tray positioned adjacent a side the first tray, and a flexible splash shield extending from a location adjacent the juncture of the first and second trays and being movable between a first position substantially covering the first tray and a second position substantially covering the second tray.

4 Claims, 1 Drawing Sheet 5,170,902

SPLASH SHIELD

This is a division of application Ser. No. 521,960, filed on May 11, 1990, now abandoned which, in turn, is a division of Ser. No. 238,717 filed Aug. 30, 1988 and now U.S. Pat. No. 4,932,552.

BACKGROUND OF THE INVENTION

The present invention relates to devices for preforming a procedure.

Devices for preforming medical procedure, such a anesthesia procedures, are known. Such devices typically have first and second trays removably received in a third tray, with the first tray having components for performing the anesthesia procedure, and the second tray having prepping components. The prepping components are utilized first in the procedure, and a problem has arisen in that the prepping solution may splash into the first tray if prepping is carried out with the second tray located in the third tray.

SUMMARY OF THE INVENTION

A principal feature of the present invention is the provision of an improved device for performing a procedure.

The device of the present invention comprises, a first tray, a second tray positioned adjacent a side of the first tray, and a flexible splash shield extending from a location adjacent the juncture of the first and second trays.

A feature of the present invention is that the shield is movable between a first position substantially covering the first tray, and a second position substantially covering the second tray.

Another feature of the invention is that the splash shield protects components in one of the trays while permitting use of the other tray.

Yet another feature of the invention is that the splash shield helps to hold components in place in the trays.

Still another feature of the invention is that in a perferred embodiment the splash shield can be readily removed when desired.

A further feature of the invention is that the splash shield may be utilized in conjunction with two trays or a single tray.

Yet another feature of the invention is the provision methods for preforming procedures by the device of the present invention.

Further features will become more fully apparent in the following description of the embodiments of this invention and from the appended claims.

DESCRIPTION OF THE PREFERRED EMBODIMENTS

Figure 1:
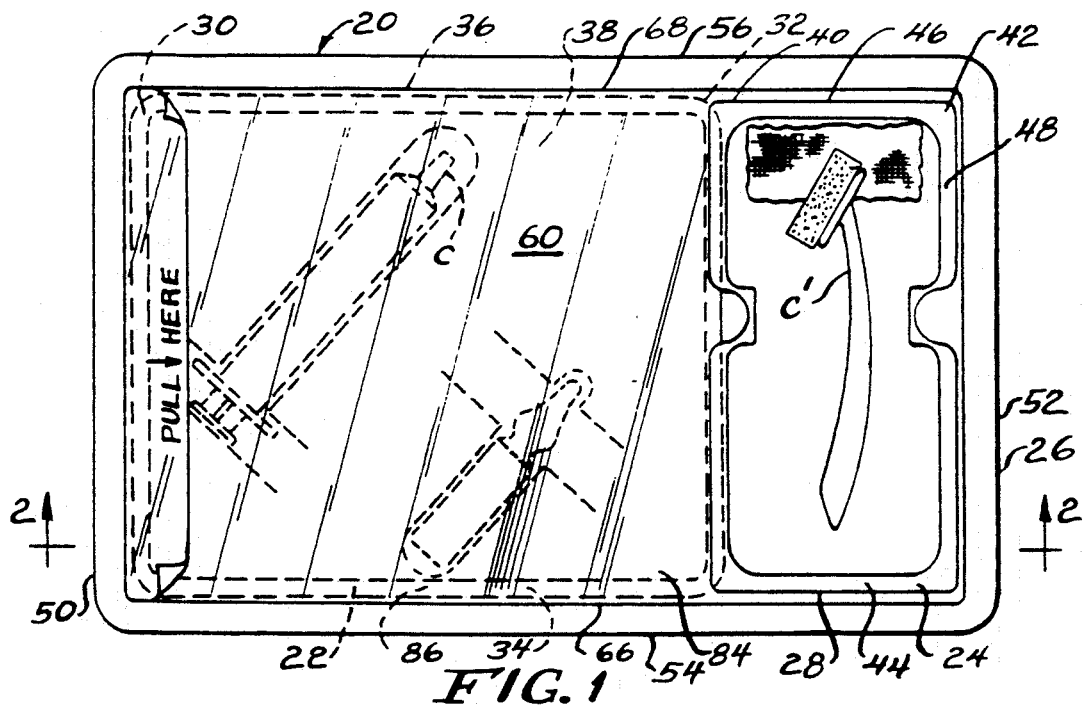
FIG. 1 is a top plan view of a device for preforming a procedure according to the present invention.
Figure 2:
FIG. 2 is a sectional view taken substantially as indicated along the line 2—2 of FIG. 1 showing a splash shield in a first covering position.

Referring now to FIGS. 1 and 2, there is shown a device generally designated 20 for performing a medical procedure, such as an anesthesia procedure. The device 20 has a first tray 22, a second tray 24, and a third tray 26, with the first and second trays 22 and 24 being removably received in a cavity 28 of the third tray 26.

The first tray 22 has opposed first and second sides 30 and 32, and opposed first and second ends 34 and 36. The first tray 22 also has a cavity 38 with a lower wall defining recesses to receive components C, such as a syringe, for performing the anesthesia procedure.

The second tray 24 has a pair of opposed first and second sides 40 and 42, and a pair of opposed first and second ends 44 and 46. The second tray 24 has a cavity 48 with a lower wall defining recesses to receive components C', such as a sponge, for prepping the patient prior to performing the anesthesia procedure.

The third tray 26 has opposed first and second sides 50 and 52, and opposed first and second ends 54 and 56. As previously discussed, the third tray 26 has a cavity 28 which removably receives the first and second trays 22 and 24 in a side-by-side relationship in the cavity 28. In a preferred form, the first tray 22 has a length between the sides 30 and 32 greated than the length of the second tray 24 between the sides 40 and 42.

The device 20 has an elongated flexible splash shield 60 which is preferably constructed from a liquid impervious material, such as a suitable transparent plastic material, or paper, as desired. The splash shield has a pair of opposed first side edges 62 and 64, respectively, and a pair of opposed first and second end edges 66 and 68, respectively, connecting the side edges 62 and 64.

In a first configuration as shown in FIGS. 1 and 2, the splash shield 60 has a first end portion 70 adjacent the edge 62 which is removably retained between a bottom wall 72 of the third tray 26 and either a bottom wall 74 of the first tray 22 or a bottom wall 76 of the second tray 24 by frictional engagement between the respective walls.

As shown, the splash shield 60 extends from a location between the bottom walls of the trays between the side 32 of the first tray 22 and the side 40 of the second tray 24 to a location over the first tray 22, with the splash shield 60 having a sufficient width and length to cover the cavity 38 of the first tray 22.

As shown, the splash shield has a second end portion 78 being folded between the side 30 of the first tray 22 and the side 50 of the third tray 26, with the second end portion 78 having a reverse fold along the fold line 80, such that an end section 82 adjacent the edge 64 extends over the first tray 22. The folded second end portion 78 is snugly received between the first and third trays 22 and 26 such that it is releasably retained in place by frictional engagement between the first and third trays and 22 and 26. In use, with reference to FIGS. 1 and 2, with the splash shield 60 in the first configuration above the first tray 22, the components C' in the second tray 24 may be utilized in order to prep the patient prior to the anesthesia procedure, while the splash shield 60 covers the components C in the first tray and prevents liquid from the second tray 24 from inadvertently passing into the covered first tray 22. In this manner, the components C in the first tray 22 are protected during use of the second tray 24. In addition, the retained splash shield 60 over the first tray 22 assists in maintaining the components C inside the first tray 22.

Figure 3:
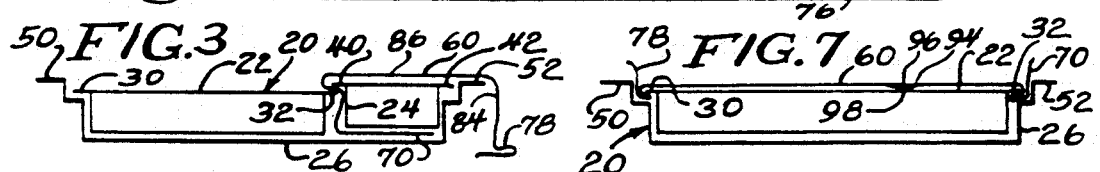
FIG. 3 is a sectional view of the device of FIG. 2 showing the splash shield in a second covering position.

Once the prepping procedure from the second tray 24 has been completed, with reference to FIGS. 2 and 3, the end section 82 of the second end portion 78, which serves as a tab, is grasped in order to pull the second end portion 78 from the location between the first tray 22 and third tray 26, and the splash shield 60 is then moved to a second configuration as shown in FIG. 3, overlying the second tray 24 while exposing the components C of the first tray 22 for use in performing the anesthesia procedure. In the second configuration of the splash shield 60, as shown in FIG. 3, in the event that prepping liquid is spilled on an outer surface 84 of the splash shield 60 in the first configuration of the splash shield 60, as shown in FIG. 2, the liquid drains back into the second tray 24 in the second configuration. In addition, an inner surface 86 of the splash shield 60 in the configuration of FIG. 2, when folded into the second configuration of FIG. 3, serves as a uncontaminated work area during performance of the anesthesia procedure utilizing the first tray 22. In this manner, the prepping and anesthesia procedures may readily be carried out while protecting the first and second trays 22 and 24 in accordance with the present invention.

Figure 6:
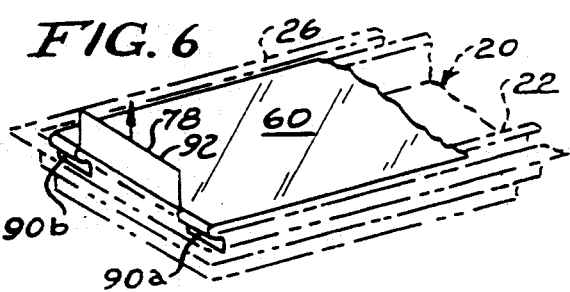
FIG. 6 is a perspective view showing one embodiment of a lift tab for the splash shield.
Figure 10:
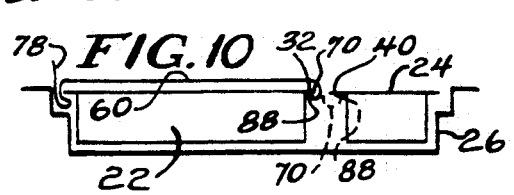
FIG. 10 is a sectional view showing another embodiment of the device of FIG. 1.

If desired, the second tray 24 may be removed from the third tray 26 in order to perform the prepping procedure, as desired by the physician, in which case the splash shield 60 may readily be removed from the device 20. However, in an alternative form of the device 20, as shown in FIG. 10, the first end portion 70 of the splash shield 60 may be permanently bonded by suitable means, such as a line 88 of adhesive, adjacent the second side 32 of the first tray 22 or the first side 40 of the second tray 24, in which case the splash shield 60 would not be removable, but would operate as previously described. Also, in an alternative form, as shown in FIG. 6, the second end portion 78 may have a pair of opposed end tabs 90a and 90b severed from a central tab 92. The end tabs 90a and 90b are removably received and frictionally engaged between the first and third trays 22 and 26, while the central tab 92 extends above the first tray 22 in order to permit removal of the end tabs 90a and b and second end portion 78 from the location between the first tray 22 and third tray 26.

Figure 4:
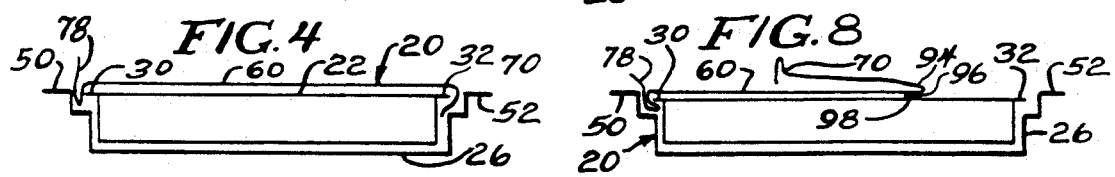
FIG. 4 is a sectional view of another embodiment of a device for performing a procedure of the present invention showing a splash shield in a first covering position.
Figure 5:
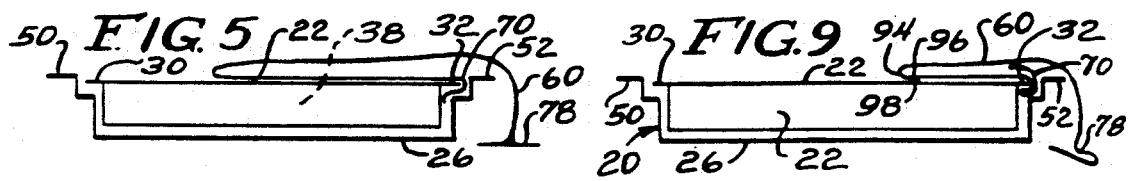
FIG. 5 is a sectional view of the device of FIG. 4 showing the splash shield in a second covering position.

Another embodiment of the device 20 of the present invention is illustrated in FIGS. 4 and 5, in which like reference numerals designate like parts. In this embodiment, the device 20 only has a first tray 22 received in a third tray 26, with both the prepping components and anesthesia components being received in the first tray 22. As shown, the first end portion 70 of the splash shield 60 is frictionally secured between the side 32 of the first tray 22 and the side 52 of the third tray 26, such that it is retained in place. The splash shield 60 has a length and width to extend over and cover the first tray 22, and the second end portion 78 is releasably retained in place between the side 30 of the first tray 22 and the side 50 of the third tray 26 in a manner as previously described in connection with FIGS. 1-3. The device 20 is shown in the covered configuration in FIG. 4.

When it is desired to utilize the device 20 of FIGS. 4 and 5, the second end portion 78 is removed from the location between the first and third trays 22 and 26, and is folded into a configuration, as shown in the FIG. 5, partially covering the first tray 22 in a region containing the anesthesia components, while exposing a portion of the first tray 22 which contains the prepping components. Thus, the prepping components may be utilized with the splash shield 60 in the second configuration, as shown in FIG. 5, in order to protect the anesthesia components during prepping the patient. After the prepping procedure has been completed, the splash shield 60 is further folded in order to expose the entire cavity 38 of the first tray 22 in order to perform the anesthesia procedure.

Figure 7:
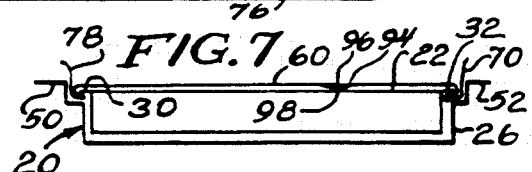
FIG. 7 is a sectional view of another embodiment of a device for performing a procedure with a splash shield in a first covering position.
Figure 8:
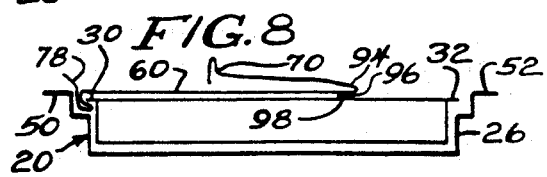
FIG. 8 is a sectional view of the device of FIG. 7 showing the splash shield in a second covering position.
Figure 9:
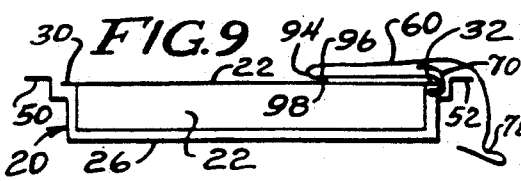
FIG. 9 is a sectional view showing the splash shield in a third covering position.

Another device 20 of the present invention is illustrated in FIGS. 7-9, in which like reference numerals designate like parts. In this embodiment, the device 20 also has only one first tray 22 removably received in a third tray 26. In this embodiment, the first end portion 70 of the splash shield 60 is folded and removably secured between the side 32 of the first tray 22 and the side 52 of the third tray 26 in a manner as previously described in connection with the second end portion 78 of the embodiment of FIGS. 1-3. Similarly, the second end portion 78 is folded and releasably retained between the side 30 of the first tray 22 and the side 50 of the third tray 26 in a manner as previously described in connection with the second end portion 78 of FIGS. 1-3. A portion 94 intermediate the first and second end portions 70 and 78 of the splash shield is secured by suitable means, such as a line 96 of adhesive to a portion 98 of the first tray 22 intermediate the sides 30 and 32. In the configuration shown in FIG. 7, the splash shield 60 extends the length and width of the first tray 22 in order to cover the first tray 22.

During use of the device 20, the first end portion 70 of the splash shield 60 is removed from the location between the first and third trays 22 and 26, and is folded over the remaining portion of the splash shield 60 in order to expose the prepping components of the first tray 22 while covering the anesthesia components of the first tray 22. Thus, the prepping procedure may be carried out with the splash shield 60 in the second configuration illustrated in FIG. 8. Once the prepping procedure has been completed, the second end portion 78 of the splash shield 60 is removed from between the first and third trays 22 and 26, and the splash shield 60 is folded towards the right, as viewed in FIG. 9, in a third configuration in order to cover the prepping portion of the first tray 22 while exposing the anesthesia components of the first tray 22 for use in preforming the anesthesia procedure. In a manner as previously described, in the second configuration of FIG. 8, the splash shield 60 protects the anesthesia components while the prepping procedure takes place, while the splash shield 60 in a third configuration as shown in FIG. 9 performs the functions in connection with covering the prepping second tray 24 as described in connection with FIGS. 1-3.

The foregoing description is given for clearness of understanding only, and no unnecessary limitations should be understood therefrom, as modifications will be obvious to those skilled in the art.

What is claimed is:

1. A tray device adapted to contain components for preforming a medical procedure on a patient, comprising:
   a first tray having opposed first and second opposed sides;
   a splash shield substantially covering the first tray and having first and second opposed end portions, a portion of the shield intermediate the opposed end portions being fixedly secured to the tray at a point intermediate the opposed sides of the tray, the opposed end portions of the shield being removably secured adjacent the opposed sides of the tray, the first end portion of the shield being foldable away from the tray at the point where the shield is fixedly secured to the tray, whereby to obtain access to a first set of components disposed within that portion of the tray uncovered by folding the first end portion of the shield; and the second end portion thereafter being foldable away from the tray at the point where the shield is fixedly secured to the tray, whereby to obtain access to a second set of components disposed within that portion of the tray uncovered by folding the second end portion;
   a second tray to receive the first tray, and in which the opposed end portions of the shield are folded between the first and second trays.

2. A device as defined in claim 1 wherein the shield is fixedly secured to the first tray by adhesive means.

3. A device as defined in claim 1 wherein the medical procedure is an anesthesia procedure, the device including first components for prepping the patient prior to administering anesthesia, and second anesthesia components.

4. The device of claim 1 wherein the opposed end portions include end sections located above the first tray.

* * * * *